United States Patent [19]

Oram et al.

[11] 4,294,239

[45] Oct. 13, 1981

[54] STEADY SUPPORT ABDOMINAL SPLINT

[76] Inventors: W. Wayne Oram, 2108 Chambwood Dr., Charlotte, N.C. 28205; Nora L. Oram, 525 Manhasset Rd., Charlotte, N.C. 28209; Robert W. Boris, 405 Bluegrass Dr., Morristown, Tenn. 37814

[21] Appl. No.: 27,766

[22] Filed: Apr. 6, 1979

[51] Int. Cl.³ .................. A61F 5/24; A61F 5/28; A61F 5/30
[52] U.S. Cl. .................. 128/96; 128/100; 128/117
[58] Field of Search ............ 128/96, 98–100, 128/111, 113, 117, 78

[56] References Cited

U.S. PATENT DOCUMENTS

| 1,286,248 | 12/1918 | Degman | 128/96 |
| 1,613,712 | 1/1927 | Manix | 128/96 |
| 2,473,136 | 6/1949 | Brose et al. | 128/96 |
| 3,578,773 | 5/1971 | Shultz | 128/96 |
| 3,945,041 | 3/1976 | Shee | 128/78 |

Primary Examiner—Robert W. Michell
Assistant Examiner—C. W. Shedd
Attorney, Agent, or Firm—Jones, Thomas & Askew

[57] ABSTRACT

A steady support abdominal splint comprises a pad shaped to conform to the human abdomen and a strap attached to the pad for wrapping around the waist of a surgery patient and holding the pad against the abdomen, thus directing pressure about and lending support to an abdominal wound of the surgery patient to prevent injury and pain to the patient as the patient coughs, breathes or otherwise uses the muscles about the abdominal wound.

2 Claims, 3 Drawing Figures

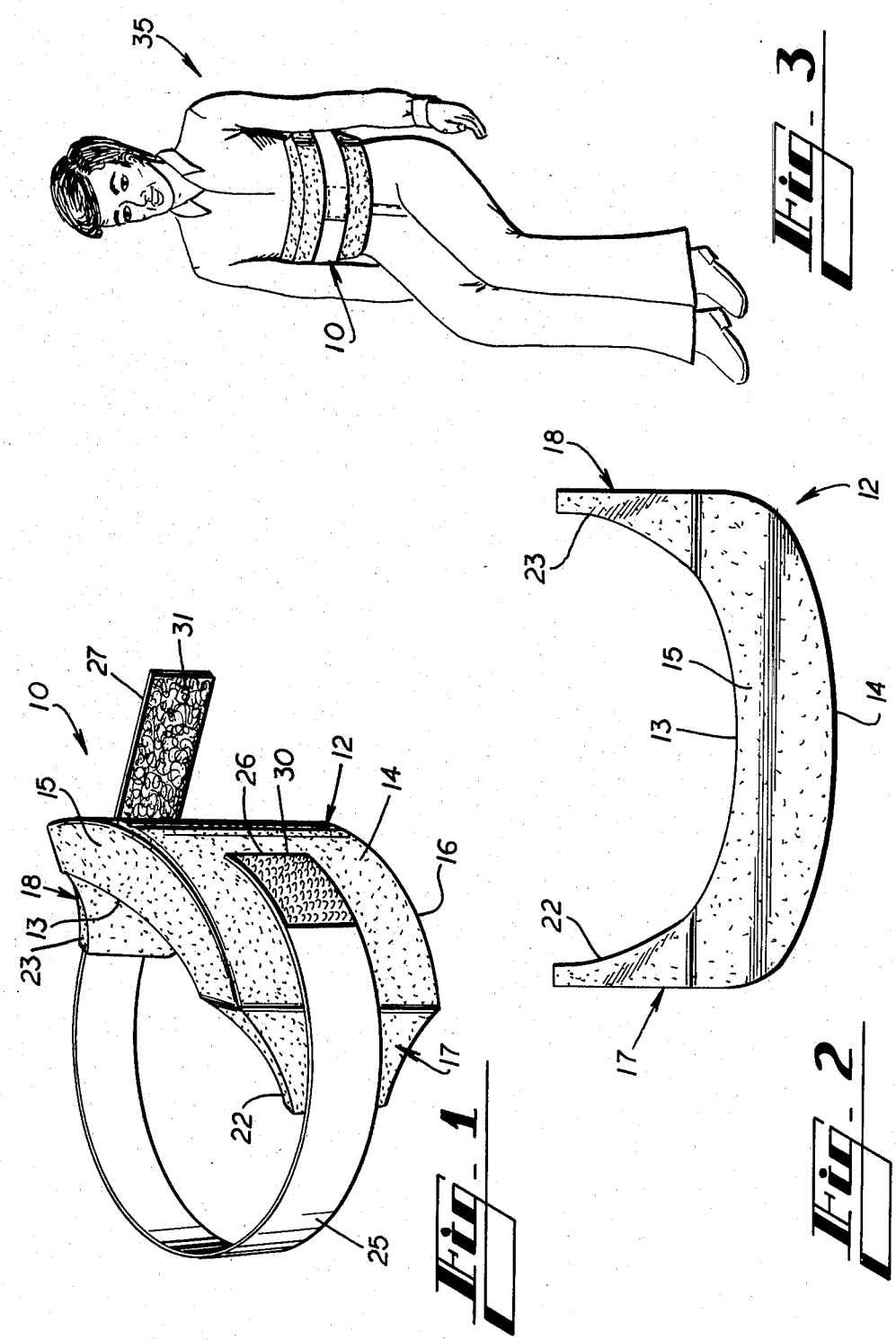

STEADY SUPPORT ABDOMINAL SPLINT

DESCRIPTION

Background of the Invention

This invention relates generally to post-surgery hospital equipment and more particularly to equipment to aid in the performance of post-operative coughing and deep breathing exercises.

Surgery patients, after they have undergone their operation, generally are confined to bed for a longer than normal period of time. As a result, the patient's body, including the blood system and lungs, require exercise to remain in good condition and to prevent problems such as pneumonia, slowing down of blood in legs and muscle weakness. These exercises include turning, leg exercises, deep breathing and coughing.

Deep breathing and coughing are necessary exercises to clear mucus which may collect in the lungs while the patient is asleep during and after surgery. If the mucus is not removed, it could possibly cause breathing problems or even pneumonia. Usually, deep breathing is done before coughing to exercise the lungs and to loosen the mucus so that it can be coughed out. After taking the deep breaths, the patient must try to cough up the mucus.

All of this deep breathing and forced coughing is quite necessary but tends to put great strain on the abdominal region. If the patient's operation site is in or near the abdominal region, a great deal of pain may result from the breathing and coughing exercises. The pain lessens the patient's desire to perform the exercises and arouses fears in the patient that he may tear stitches or cause other complications.

To counteract the patient's pain and fear and to prevent damage to the patient's abdominal wound, it has been the practice in hospitals to advice a patient to hold pressure against his abdomen at the wound with a pillow or other soft object or with his hand as he coughs. The pillow is pressed against the abdomen at the wound and tends to reinforce the area at the wound and assist the muscles about the wound to resist the strain of coughing. Oftentimes the patient cannot maneuver enough or is too weak to apply this pressure and the aid of a nurse is required. Also, adequate and timely pressure and support cannot always be accomplished by using a pillow and/or the patient's arms and hands, and a nurse is not always available to assist the patient.

Summary of the Invention

Briefly described, the present invention comprises an abdominal splint for directing pressure about and lending support to an abdominal wound of a surgery patient for preventing injury and pain to the patient as the patient coughs, breaths or otherwise uses the muscles about the abdominal wound. The splint includes a pad of sturdy, yet resilient material formed to a shape and size sufficient to cover a substantial portion of the human abdomen. The splint is held against the abdomen, in the preferred case, by a strap, and the surface of the pad which is held adjacent the body of the patient is concave and shaped to fit the normal contours of the stomach.

The pad of the splint is sufficiently rigid to hold its shape and to provide "support pressure", as later described, generally to the abdomen over the entire surface area of the pad. Yet, the pad is resilient enough to transmit "localized pressure", as later described, through the pad to localized regions of the abdomen without lessening the support pressure provided generally by the pad.

The strap attached to the pad of the splint is attached at one of its ends to the front of the pad and is of sufficient length to wrap around the back and then again to the front of the patient, so that the free end overlaps the attached end about the pad in front of the patient. This permits the patient to tighten and loosen the splint without requiring the patient to reach behind his back. Since the splint is strapped to the body of the patient, an invalid patient need not be concerned with maneuvering the splint and holding the splint in place. By providing an appropriate strap connector, even a patient with only one free arm can tighten or loosen the strap to increase or relieve the support pressure provided by the pad. Thus, the splint lessens the need for frequent adjustment by nurses. Furthermore, since the splint is constructed so that it can be attached to the abdomen of the patient, the arms of the patient are not required to hold the splint in place and the patient's hands, if available, can be used as necessary to apply localized pressure through the splint.

The flexible, yet sturdy pad of the splint is of greater density than the typical pillow. Therefore, pressure and support are more uniformly distributed about the abdomen by the splint of the present invention than by a pillow or even by arms stretched across the waist.

Therefore, it is an object of the present invention to provide an abdominal splint which will give steady support to the abdomen of a surgery patient.

Another object of the invention is to provide a steady support abdominal splint which will alleviate the need for constant attention for post-surgery patients.

Yet another object of the invention is to provide an abdominal splint which provides comfort and support to the abdomen of the human body for post-operative coughing and deep breathing exercises.

Still another object of the invention is to provide a steady support abdominal splint which allows for the application of localized pressure to a wound at the human abdomen while maintaining steady support pressure to the abdomen.

Another object of the invention is to provide a steady support abdominal splint which can be worn by a patient and allows the patient to lie on his stomach to position the patient for postural drainage and chest percussion.

Other objects, features and advantages of the present invention will become apparent upon reading and understanding the remaining specification when taken in conjunction with the accompanying drawings.

BRIEF DESCRIPTION OF THE DRAWINGS

FIG. 1 is a pictorial view of the steady support abdominal splint according to the present invention.

FIG. 2 is a top view of the abdominal splint in FIG. 1, with the belt removed.

FIG. 3 is a pictorial view of the abdominal splint of FIG. 1 as used by a post-surgery hospital patient.

DETAILED DESCRIPTION

Referring now in more detail to the drawings in which like numerals represent like components throughout the several views, FIG. 1 shows the steady support abdominal splint 10 of the present invention. The splint 10 comprises a pad 12 including a semicircular or concave back side 13, a convex front side 14, a top edge 15, a bottom edge 16 and two end portions 17, 18. Each end portion 17, 18 tapers off to form a tab section 22, 23 protruding rearwardly from the back side 13. A belt or strap 25 is attached at one of its ends 26 to the front side 14 of the pad 12 and is of length sufficient to encircle the waist of a human body (FIG. 3) and the pad 12. An adherent strip 30 is attached to the end 26 of the belt 25 and comprises a plurality of flexible hooks defined throughout the strip 30. A second, longer adherent strip 31 is attached along the belt 25 at the free end 27 of the belt and comprises a plurality of flexible loops defined throughout the strip 31. These adherent strips 30, 31 cooperate to function as a buckling device by which the belt 25 can be easily adjusted to encircle different diameters. One example of such cooperating adherent strips of material is commercially available under the trademark "Velcro". The length of the second strip 31 will vary depending upon the range of different belt diameters desired.

The back surface 13 of the pad 12 is semicircular in configuration to fit the general contour of the abdomen of the human body. The configuration of the back side 13 is more desirably concave to more closely conform to the abdomen. The distance between the two tab sections 22, 23 corresponds to the width across the abdomen of the human body (see FIG. 3).

The pad 12 is preferably molded and is formed of a resilient, yet sturdy material which will retain the shape into which it is molded, or otherwise formed, over a long period of time, and which is resilient enough to be deformed by pressure to transmit force directly through the pad and then return to its original formed shape. As example of a pad 12 usable as part of the splint is a two and one half inches thick, thirteen inches wide and eight and one half inches high pad with two and one half inches long tab sections 22, 23, of molded foam rubber having a density of 3.0±0.5 pounds per cubic foot.

This particular thickness and density of the pad causes the pad to be sufficiently pliable to enable the patient to apply localized pressure to a wound in the abdomen by pressing with his hands against the outside surface of the pad. If the density of the pad is increased, the thickness of the pad can be decreased to retain the desired flexibility of the pad.

A preferred material for the present invention is a middle to high density, high resilient "HR" cellular foam, for example, a foam rubber having a density ranging from 2.5 to 3.5 pounds per cubic foot with an indentation load deflection of from 25 to 35 pounds-force per fifty square inches area for twenty-five percent deflection, as set forth in ASTM D1564.

When being used (see FIG. 3), the splint 10 is worn by a post-surgery patient 35 with the pad 12 at the front of the body torso and the back surface 13 of the pad placed against the abdomen. The tab sections 22, 23 of the pad end portions 17, 18 extend rearwardly along the patient's sides. The belt 25 is wrapped around the body torso and about the front surface 14 of the pad 12 and drawn to desired tightness, and the belt ends 26, 27 are buckled together by joining together the adherent strips 30, 31. The rearwardly projecting tab sections 22, 23 provide an extension of the pad to the sides of the body and comfort to the patient but the radius of curvature of the inside surface of the pad and its tab sections is not critical to the proper splinting and supporting functions of the splint 10 because when the strap is wrapped about the patient, tightened and connected at the front of the patient, the inside surface of the pad will be urged into conformity with the shape of the abdomen of the patient.

With the splint 10 in position, the patient 35 can begin his deep breathing and coughing exercises. If the patient is experiencing too much discomfort, he may apply pressure to the abdomen, utilizing the splint 10, to aid in alleviating his discomfort. The abdominal splint 10 as disclosed herein is used in two ways to apply pressure to the abdomen. First, pressure is applied generally to a large portion of the abdomen by approximately the entire back surface 13 of the pad 12, which contacts the abdomen of the patient, by unbuckling the belt 25, pulling on the free end 27 to shorten the diameter of the belt and to draw the pad tighter against the abdomen, and rebuckling the ends 26, 27 of the belt. This first pressure is referred to herein as "support pressure" as it lends general support to the abdomen to ease discomfort. The support pressure may be increased or decreased by tightening or loosening the strap. Second, more direct pressure is applied by the patient, or by an aide, about a wound or other specific "local" region on the abdomen by applying added force against the outer surface, or front side 14, of the splint 10 inwardly toward the abdomen, as for example force applied by a hand of the patient or a nurse against the outer surface 14 of the splint toward the patient's abdomen. This second pressure is referred to herein as "localized pressure", and by putting force against a particular region of the outer surface 14 of the resilient pad, the pressure is spread to some extent from the point of application against the outside surface of the pad but is transmitted more directly through the pad to the "local" region directly opposite the point of external force.

While this invention has been herein described with particular detail to a preferred embodiment thereof, it will be understood that variations and modifications can be effected within the spirit and scope of the invention as described hereinbefore and as defined in the appended claims.

We claim:

1. A splint supporting the front abdomen of a human body and directing pressure to localized regions of the abdomen of a human body, comprising a molded pad of resilient material formed in an approximate U-shape with a front portion of substantially uniform thickness and height and including top edge, bottom edge, convex outer surface, concave body facing surface, and opposite end portions, said end portions being curved with respect to said front portion to extend partially about the sides of the abdomen of the human body, said front portion merging into said end portions and each end portion symmetrically diminished in height and the outer surface of each end portion tapered toward its body facing surface whereby the thickness of each end portion is diminished, said body facing surface being of a width sufficient to span the width of the human body across the abdomen and said pad being of a height sufficient to approximately cover the abdominal area of the body without extending over the thorax and formed in a size and shape along said body facing surface for conforming to the shape of the front abdominal area of the human body, the material of said pad having a density of between 2.5 and 3.5 pounds per cubic foot and a load bearing (ILD) of a twenty-five percent load deflection value at between 25 and 35 pounds, strap means for extending from said end portions and about the abdomen to urge said pad in constant contact with the abdomen to apply approximately uniform support pressure to the abdomen, said end portions being of a height at least as wide as said strap means, said pad being fabricated of material sufficiently flexible to permit a force applied externally to the pad to transmit localized pressure through the pad to the abdomen, whereby the pad is held by the strap against the abdomen and the wearer can press inwardly with his hand against the outside surface of the pad when coughing to apply additional pressure to a localized area of the abdomen.

2. The splint of claim 1, wherein said strap means extends from the front side of said pad about an end portion, then about the back of the human body, then about the other end portion back to the front side of said pad with the ends of said strap means connected together at the front side of said pad.

* * * * *